United States Patent [19]

Tucker et al.

[11] 3,962,245

[45] June 8, 1976

[54] DIALKYLSULFONAMIDE DYES

[75] Inventors: Robert Jerome Tucker, Hackettstown; Richard Spector, Kendall Park, both of N.J.

[73] Assignee: American Cyanamid Company, Stamford, Conn.

[22] Filed: Jan. 16, 1975

[21] Appl. No.: 541,546

Related U.S. Application Data

[62] Division of Ser. No. 431,199, Jan. 7, 1974, Pat. No. 3,909,442.

[52] U.S. Cl. ............................................ 260/256.5 R
[51] Int. Cl.$^2$ ....................................... C07D 239/00
[58] Field of Search ............................. 260/256.5 R

[56] References Cited
OTHER PUBLICATIONS

Chemical Abstracts, 67: 12529a (1967).

*Primary Examiner*—Leonard Schenkman
*Attorney, Agent, or Firm*—John L. Sullivan

[57] ABSTRACT

Novel dyes for plastic substrates which act as filters in such substrates for argon and double-frequency neodymium laser beams are sulfonamide derivatives of 12-H-naphthoperinone. These dyes are soluble in and compatible with the plastic substrate and provide stability to ultraviolet light.

2 Claims, No Drawings

DIALKYLSULFONAMIDE DYES

This is a division of application Ser. No. 431,199, filed Jan. 7, 1974, now U.S. Pat. No. 3,909,442, issued Sept. 30, 1975.

This invention relates to novel compositions of matter. More particularly the invention relates to dialkylsulfonamide derivatives of 12-H-phthaloperinone, which derivatives are useful orange colorants for plastic materials.

In the preparation of various types of plastic optical filter or screening materials, dyes with certain spectral characteristics are often required so that the required spectral or light absorbing properties may be obtained in the particular filters or screens being prepared. To be useful in such applications, the dyes must be soluble in and compatible with the plastic substrate so that the dye does not migrate to the surface of the plastic and exhibit blooming, or crystallization. In addition, the dye must also possess stability to light so as to provide a useful service life for the plastic filter or screen.

In accordance with the present invention, there is provided an orange or yellow colored dye of the general formula

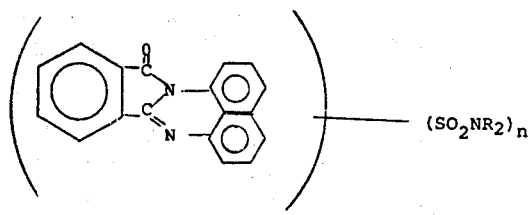

wherein R is an alkyl of 1 to 5 carbon atoms and $n$ is an integer of 1 to 4.

The dyes of the present invention are improved in solubility, compatibility, and stability in plastic substrates, particularly in polyvinyl chloride, over prior art materials.

In preparing the novel compositions of the present invention, the starting material is conveniently 12-H-phthaloperinone, which is commercially available as Aminoplast Orange LFP.

Reaction is carried out to introduce N,N-dialkylsulfonamide radicals on the 12-H-phthaloperinone moiety in accordance with conventional procedures for such radicals on other moieties. Generally the reaction is carried out by treating the intermediate with chlorosulfonic acid under conditions which preferably introduce two sulfonyl chloride radicals on the 12-H-phthaloperinone moiety and then subsequent reaction with a dialkyl amine is carried out to provide the N,N-dialkyl-sulfonamide radicals.

Substitution of the 12-H-phthaloperinone will occur at the various reactive sites of the phenyl and naphthyl ring portions of its structure. Actual positions substituted will vary depending upon reaction conditions employed and the amounts of reagents used in effecting substitution. Under the usual conditions employed in preparing the compound wherein $n$ is 2, substitution on the naphthyl ring portion of the molecule predominates. It can be appreciated that on a statistical basis, a wide variety of positions can be occupied by the N,N-dialkylsulfonamide groups introduced and, therefore, the invention is not limited to any specific positions occupied by the N,N-dialkylsulfonamide groups. Thus, it is possible that the product obtained in any given sulfonamidation reaction will be mixed with respect to the positions occupied by the sulfonamide groups and with respect to the specific number of substituents present on a given molecule. However, an average number of substituents and a predominating substituent arrangement will prevail in most cases. The effectiveness of the compounds does not appear to be influenced by the particular species involved.

12-H-phthaloperinone is the required starting material and no equivalents are known. This intermediate is chlorosulfonated in accordance with conventional procedures, such as those described in U.S. Pat. Nos. 2,897,207 and 3,536,502 wherein sulfonamidation of phthalocyanine derivatives is disclosed.

After chlorosulfonation is effected, amidation is carried out using a suitable dialkylamine. Suitable dialkylamine are those containing alkyl groups of 1 to 5 carbon atoms. Typical amines are dimethylamine, diethylamine, the dipropylamines, the dibutylamines, and the diamylamines. The amount of dialkylamine used is generally sufficient to effect complete amidation of the chlorosulfonate groups introduced. The number of chlorosulfonate groups introduced will generally vary from 1 to 4 per mole of 12-H-phthaloperinone, with 2 being preferred. Conditions of reaction are sufficient to introduce the desired number of substituents and excesses of sulfonyl chloride and amine may be employed.

The dyes of the present invention are especially useful for coloring plastics, especially polyvinyl chloride, and because of their spectral characteristics, are useful in plastic compositions applicable as protective filters against argon and double-frequency neodymium laser beams. The dyes are used at effective levels in such uses and will dye the plastic yellow to orange shades, depending upon the effective level employed. Typically, a usage level in the range of about 0.1 to 2.0%, based on the weight of plastic may be used but other usage levels may be employed so long as effective filtering is obtained. In addition to polyvinyl chloride, one may use such plastics are polvinylidene chloride, polyvinyl bromide, polyvinylidene bromide, polytrifluoroethylene, polytetrafluoroethylene, polyacrylonitrile, polystyrene, polymethyl methacrylate, and the like.

The invention is more fully illustrated by the examples which follow.

EXAMPLE 1

Preparation of Bis(N,N-dibutylsulfonamido)-12-H-phthaloperinone

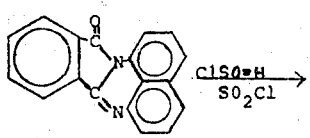 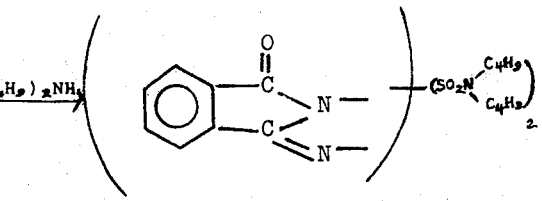

To 195 grams of chlorosulfonic acid were added gradually with stirring 32.4 grams of 12-H-phthaloperinone. The mixture was heated to 130°C. over a period of 2 hours after which it was cooled to room temperature. Then 30 milliliters of thionyl chloride as added dropwise and the solution was heated at 80°C. for 2 hours.

After standing overnight, the reaction mixture was drowned in 900 milliliters of ice-water with 132 grams sodium chloride added, maintaining the temperature a 0°C. by addition of ice as necessary. The disulfonyl chloride substituted intermediates which precipitated was isolated by filtration and washed with ice-water.

The solid intermediate was then reacted with butylamine. The orange intermediate was suspended in a mixture of 900 ml. of water and 600 g. ice. To the mixture, 210 ml. di-n-butylamine was added, followed by 60 g. sodium bicarbonate and 300 ml. acetone. After stirring vigorously for 1 hour the gummy solid which had formed was isolated by filtration and then dissolved in anhydrous ethanol. To the solution was added 3 liters of water containing 100 grams of sodium chloride and 50 ml. concentrated hydrochloric acid. After stirring further, the gummy residue was removed and dissolved in anhydrous ethanol and clarified. An orange solid precipitated, was removed and recystallized once from anhydrous ethanol to yield the product bis(N,N-dibutylsulfonamide)-12-H-phthaloperinone.

EXAMPLE 2

Polyvinyl Chloride Composition

A polyvinyl chloride chip was prepared which weighed 50 grams and as of a thickness of 57 mils. In the chip as prepared was incorporated 0.265 gram of the dye of Example 1 and 0.13 gram of 2,2'-dihydroxymethoxybenzophenone.

The chip was subjected to examination to determine luminous transmission (Y value) and optical density (O.D.) at 488, 514.5, and 530 nanometers. It was then exposed to ultraviolet light in a Fade-ometer and observed for compatibility and optical density. The following results were obtained.

| $\lambda$(nm.) | O.D. | |
|---|---|---|
| 488[1] | 8.5 | |
| 514.5[2] | 5.0 | Y=49% |
| 530[3] | 2.4 | |

[1]Wavelength of argon ion laser
[2]Wavelength of argon ion laser
[3]Wavelength of double neodymiun laser After 500 hours Fade-ometer exposure, the chip was in excellent condition and the optical density values had not changed. After 7 months, the chip still exhibited no signs of incompatibility of contents.

COMPARATIVE EXAMPLE A

Following the procedure of Example 2, a similar chip was prepared employing in place of the dye of Example 1, an equal amount of 12-H-phthaloperinone.

Upon exposure of the chip to ultraviolet light in the Fade-ometer for 3 hours, the dye exhibited blooming and exuding from the plastic, illustrating a high level of incompatability.

EXAMPLE 3

Polyvinyl Chloride Composition

The procedure of Example 2 was followed in every material detail except that 0.6 gram of the dye of Example 1 was employed instead of 0.265 gram and the chip thickness was 54 mils. Examination of the chip gave the following results:

| $\lambda$(nm.) | O.D. | |
|---|---|---|
| 488 | 46 | |
| 514.5 | 18 | Y=49% |
| 530 | 10 | |

After 1000 hours exposure in the Fade-ometer, the sample was unchanged. Afte 4.5 months, no compabitility problem was detected.

EXAMPLES 4–11

Following the procedure of Example 1 a series of N,N-dialkylsulfonamide derivatives of 12-H-phthaloperinone are prepared. The various derivatives are listed below.

| EXAMPLE | ALKYL | n |
|---|---|---|
| 4 | methyl | |
| 5 | ethyl | 2 |
| 6 | ethyl | 3 |
| 7 | n-propyl | 2 |
| 8 | iso-propyl | 2 |
| 9 | amyl | 2 |
| 10 | amyl | 1 |
| 11 | methyl | 4 |

EXAMPLE 12

Following the procedure of Example 2 each of the compounds of Examples 4–11 are evaluated in polyvinyl chloride chips. In each instance substantially the same results as exhibited by the dye of Example 1 are obtained.

We claim:
1. A compound of formula

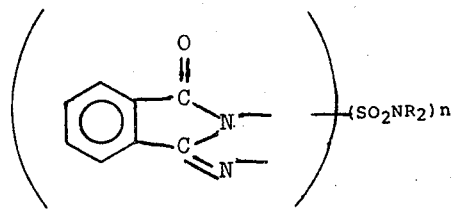

wherein R is an alkyl group of 1–5 carbon atoms and $n$ is an integer of 1–4.

2. The compound of claim 1 wherein R is n-butyl and $n$ is 2.

* * * * *